(12) United States Patent
Brown

(10) Patent No.: US 10,864,182 B2
(45) Date of Patent: Dec. 15, 2020

(54) TREATMENT OF FRAGILE X SYNDROME

(71) Applicant: Healx Limited, Cambridge (GB)

(72) Inventor: David Brown, Cambridge (GB)

(73) Assignee: Healx Limited

( * ) Notice: Subject to any disclaimer, the term of this patent is extended or adjusted under 35 U.S.C. 154(b) by 0 days.

(21) Appl. No.: 16/383,028

(22) Filed: Apr. 12, 2019

(65) Prior Publication Data

US 2019/0314308 A1     Oct. 17, 2019

Related U.S. Application Data

(60) Provisional application No. 62/657,209, filed on Apr. 13, 2018.

(30) Foreign Application Priority Data

Apr. 13, 2018 (EP) ..................................... 18167346

(51) Int. Cl.
| | |
|---|---|
| *A61K 31/19* | (2006.01) |
| *A61K 31/192* | (2006.01) |
| *A61P 25/00* | (2006.01) |
| *A61K 9/00* | (2006.01) |

(52) U.S. Cl.
CPC .......... *A61K 31/192* (2013.01); *A61K 9/0053* (2013.01); *A61P 25/00* (2018.01)

(58) Field of Classification Search
CPC .................................................. A61K 31/192
USPC ........................................ 514/568, 569, 570
See application file for complete search history.

(56) References Cited

U.S. PATENT DOCUMENTS

2019/0314309 A1    10/2019   Brown

FOREIGN PATENT DOCUMENTS

| CN | 103622941 A | * | 3/2014 |
|---|---|---|---|
| WO | WO-2008/021210 A2 | | 2/2008 |
| WO | WO-2019/197632 A1 | | 10/2019 |

OTHER PUBLICATIONS

Bhogal et al., "Fragile X syndrome and model organisms: identifying potential routes of therapeutic intervention," Dis Model Mech, 3(11-12): 693-700 (2010).
Extended European Search Report issued by the European Patent Office in corresponding Application No. EP 18167346.8 dated Aug. 17, 2018.
Farshbaf et al., "Peroxisome proliferator activated receptor gamma (PPARgamma) as a therapeutic target for improvement of cognitive performance in Fragile-X," Med Hypotheses, 82(3):291-294 (2014).
Felts et al., "Sulindac Derivatives That Activate the Peroxisome Proliferator-activated Receptor gamma but Lack Cyclooxygenase Inhibition," J Med Chem, 51(16):4911-4919 (2008).
Healx: "Fragile X Syndrome Drug Repurposing Summary Report," Retrieved from the Internet, URL: https://www.fraxa.org/wp-content/uploads/2017/06/Healx-Summary-Report_FRAXA_June-2017.pdf [retrieved on Aug. 3, 2018].
Levin, "Drug Repurposing Study Results Accelerate Progress Towards Fragile X Treatments," Fraxa Research Foundation, Published Oct. 29, 2017. Accessed online Apr. 19, 2018:https://www.fraxa.org/drug-repurposing-accelerates-progress-towards-fragile-x-treatments/.

(Continued)

*Primary Examiner* — Shengjun Wang
(74) *Attorney, Agent, or Firm* — Foley Hoag LLP

(57) ABSTRACT

Described herein is the use of sulindac in the treatment of fragile X syndrome (FXS).

17 Claims, 1 Drawing Sheet

(56) References Cited

OTHER PUBLICATIONS

Zhang et al., "Downregulating the Canonical Wnt/ß-catenin Signaling Pathway Attenuates the Susceptibility to Autism-like Phenotypes by Decreasing Oxidative Stress," Neurochem Res, 37(7):1409-1419 (2012).

Dairum, "Non-steroidal anti-inflammatory agents, tolmetin and sulindac attenuate quinolinic acid (QA)-induced oxidative stress in primary hippocampal neurons and reduce QA-induced spatial reference memory deficits in male Wistar rats," Life Sciences 80:1431-1438 (2007).

Huguet et al., "The Genetic Landscapes of Autism Spectrum Disorders," Annual Review of Genomics and Human Genetics, 14:191-213 (2013).

Maurin, "Fragile X Syndrome: From molecular pathology to therapy," Neuroscience and Biobehavioral Reviews, 46:242-255 (2014).

\* cited by examiner

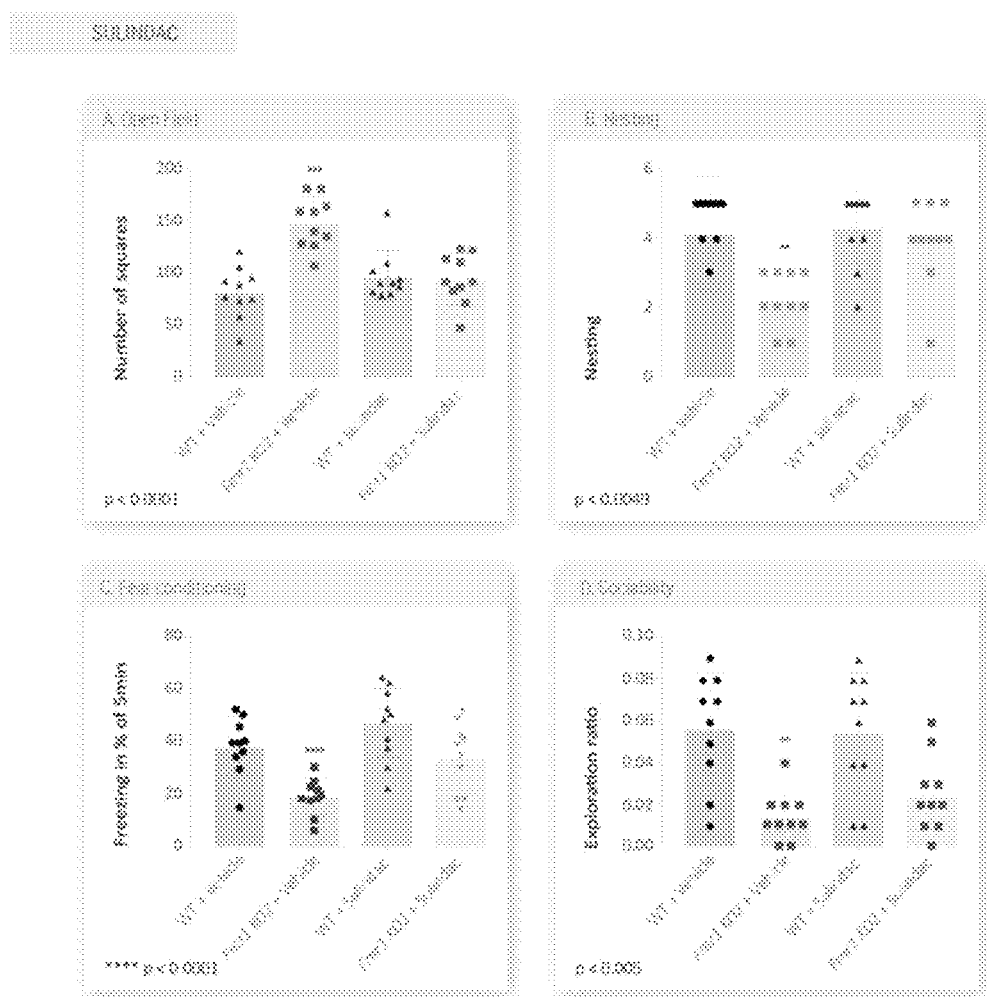

TREATMENT OF FRAGILE X SYNDROME

CROSS-REFERENCE TO RELATED APPLICATIONS

This application claims the benefit of U.S. Provisional Application No. 62/657,209, filed on Apr. 13, 2018, and European Application No. EP18167346.8, filed on Apr. 13, 2018. The entire teachings of the above applications are incorporated herein by reference.

FIELD OF THE INVENTION

This invention relates to the use of sulindac in the treatment of fragile X syndrome (FXS).

BACKGROUND OF THE INVENTION

Fragile X syndrome, often referred to as fragile X, is the most common inherited cause of intellectual impairment and the most common monogenic cause of autism. It affects around 1 in 4000 males and 1 in 6000 females worldwide.

There are a wide range of characteristics associated with fragile X, and typically males are more affected than females. One of the major characteristics associated with fragile x syndrome is intellectual impairment, such as difficulties with cognitive, executive and language performance. Individuals with fragile x syndrome typically have social anxiety characterised by social, emotional and communication difficulties related to extreme shyness, poor eye contact and challenges forming peer relationships. Fragile x syndrome is also associated with hyperactivity and disruptive behaviour, such as short attention span, distractibility, impulsiveness, restlessness, over-activity and sensory problems. Furthermore, individuals with fragile x syndrome often suffer from seizures.

Fragile x syndrome arises from a mutation in a single gene called Fragile X Mental Retardation Gene 1 (FMR1). The 5' UTR of FMR1 contains a CGG trinucleotide repeat that is polymorphic in the population. Once the repeats exceed 200 in number, methylation of the promoter is triggered, and this in turn causes the lack of expression of the gene and translation of its encoded protein, the Fragile X Mental Retardation Protein (FMRP). FMRP is an RNA-binding protein involved in different steps of mRNA metabolism, such as translational control (in soma and dendritic spines) and RNA transport.

At present, there is no effective therapy to treat fragile x syndrome. However, there have been considerable efforts to identify pharmacological targets to treat this disorder. In particular, fragile x syndrome has been a frequent target of repurposing efforts as well as repositioning of drugs in development. Many different standards and methods have been applied to this task. In many cases, repurposing candidates have been identified based primarily on clinical pattern matching, while in others basic disease mechanisms have been studied extensively to identify therapeutic targets, followed by thorough preclinical validation.

Overall, efforts to treat fragile x syndrome have led to some exciting possibilities, but no definitive successes, despite much effort. This has highlighted the need for new therapies.

Sulindac is a non-steroidal anti-inflammatory drug (NSAID). Sulindac is used in the treatment of acute and chronic inflammatory conditions, such as arthritis, shoulder bursitis and tendonitis, as it exhibits anti-inflammatory, analgesic and antipyretic activities. Like other NSAIDs, the mechanism of action of sulindac is not fully understood. However, it is thought to be related to prostaglandin synthetase inhibition.

Sulindac is a yellow crystalline compound, and is a weak organic acid practically insoluble in water below pH 4.5, but very soluble as the sodium salt or in buffers of pH 6 or higher. Following absorption, sulindac undergoes two major biotransformations (i) reversible reduction to the active sulphide metabolite, and (ii) irreversible oxidation to the inactive sulfone metabolite. Sulindac has the systematic name (Z)-5-fluoro-2-methyl-1-[[p-(methylsulfinyl)phenyl]methylene]-1H-indene-3-acetic acid.

Sulindac is marketed as CLINORIL®, in 200 mg tablets for oral administration. The tablets contain sulindac, cellulose, magnesium stearate, and starch. CLINORIL® is used to treat osteoarthritis, rheumatoid arthritis, ankylosing spondylitis, acute subacromial bursitis/supraspinatus tendinitis and acute gouty arthritis. A typical dosage is 150 mg to 200 mg twice per day.

SUMMARY OF THE INVENTION

In certain embodiments, the present invention relates to sulindac, or a pharmaceutically acceptable salt thereof, for use in the treatment of fragile x syndrome. As will be evident from the in vivo data presented below, sulindac is effective in treating fragile x syndrome. Chronic treatment with sulindac significantly improved the Fmr1 KO2 mouse phenotype, fully rescuing open field and nesting behaviour, while partially rescuing contextual fear conditioning and sociability. This is evidence that sulindac is useful in the therapy of fragile x syndrome.

A first aspect of the invention is sulindac, or a pharmaceutically acceptable salt thereof, for use in the treatment of fragile x syndrome.

A second aspect of the invention is provided use of sulindac, or a pharmaceutically acceptable salt thereof, for the manufacture of a medicament for use in the treatment of fragile x syndrome.

A third aspect of the invention is provided a method of treating fragile x syndrome comprising administering to a subject in need thereof a therapeutically effective amount of sulindac or a pharmaceutically acceptable salt thereof.

DESCRIPTION OF THE FIGURES

FIG. 1A-FIG. 1D show the results from sulindac in vivo testing.

DETAILED DESCRIPTION

As fragile x is a syndrome, there are a number of different manifestations and symptoms in patients (or "subjects"). These include; intellectual impairment, such as difficulties with cognitive, executive and language performance, short-term memory, executive function, visual memory and visual-spatial relationships; autism; social anxiety (i.e., difficulties in social interaction) such as poor eye contact, gaze aversion, prolonged time to commence social interaction, and challenges forming peer relationships; hyperactivity and repetitive behaviour, including very short attention spans, hypersensitivity to visual, auditory, tactile, and olfactory stimuli, distractibility, impulsiveness, restlessness and over-activity; disruptive behaviour, including fluctuating mood, irritability, self-injury and aggression; obsessive compulsive disorder (OCD); ophthalmologic problems, such as strabismus; seizures; difficulties with working memory, which involves the temporary storage of information while processing the same or other information; difficulties with phonological memory (or verbal working memory); and fragile X-related primary ovarian insufficiency (FXPOI).

In the present invention, and as demonstrated by the below in vivo data, sulindac is used to treat one or more of the above symptoms, and is therefore an effective treatment of fragile x syndrome. Preferably, sulindac is used for the treatment of fragile x syndrome, wherein the patient is exhibiting typical symptoms of the syndrome including social anxiety, hyperactivity, memory loss and/or disruptive behaviour. More preferably, sulindac is used for the treatment of fragile x syndrome, wherein the patient is exhibiting hyperactivity, memory loss and/or disruptive behaviour.

The term "hyperactivity" has its normal meaning in the art. Hyperactivity may include having very short attention spans, hypersensitivity to visual, auditory, tactile, and olfactory stimuli, distractibility, impulsiveness, restlessness and/or over-activity.

The term "social anxiety" has its normal meaning in the art. It may also be termed as difficulties in social interaction or low sociability. Social anxiety may include having poor eye contact, gaze aversion, prolonged time to commence social interaction, social avoidance or withdrawal and challenges forming peer relationships.

The term "memory loss" has its normal meaning in the art. It may also be called memory impairment. It refers to an inability to retain information either short-term or long-term. It may include difficulties with cognitive, executive and language performance, executive function and visual memory. It may also include difficulties with working memory, also called short-term memory (i.e. the temporary storage of information while processing the same or other information) and difficulties with phonological memory (or verbal working memory).

The term "disruptive behaviour" has its normal meaning in the art. It may also include repetitive behaviour. It may also include fluctuating mood, irritability, self-injury and aggression.

It is known that sulindac undergoes two major biotransformations following absorption (i) reversible reduction to the active sulphide metabolite, and (ii) irreversible oxidation to the inactive sulfone metabolite. However, the mechanism by which sulindac treats fragile x syndrome is not yet known. Therefore, for the avoidance of doubt, any reference to sulindac also embraces its metabolites (both the sulphide and sulfone metabolites).

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

In the present invention, sulindac may be administered in a variety of dosage forms. In one embodiment, sulindac may be formulated in a format suitable for oral, rectal, parenteral, intranasal or transdermal administration or administration by inhalation or by suppository.

Sulindac may be administered orally, for example as tablets, troches, lozenges, aqueous or oily suspensions, dispersible powders or granules. Preferably, sulindac is formulated such that it is suitable for oral administration, for example tablets and capsules.

Sulindac may also be administered parenterally, whether subcutaneously, intravenously, intramuscularly, intrasternally, transdermally or by infusion techniques. Sulindac may also be administered as suppositories.

Sulindac may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed.

The present invention also provides an inhalation device containing sulindac. Typically said device is a metered dose inhaler (MDI), which contains a pharmaceutically acceptable chemical propellant to push the medication out of the inhaler.

Sulindac may also be administered by intranasal administration. The nasal cavity's highly permeable tissue is very receptive to medication and absorbs it quickly and efficiently. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing sulindac.

Sulindac may also be administered by transdermal administration. For topical delivery, transdermal and transmucosal patches, creams, ointments, jellies, solutions or suspensions may be employed. The present invention therefore also provides a transdermal patch containing a sulindac.

Sulindac may also be administered by sublingual administration. The present invention therefore also provides a sub-lingual tablet comprising sulindac.

Sulindac may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

In an embodiment of the invention, sulindac is administered in an effective amount to treat the symptoms of fragile x syndrome. An effective dose will be apparent to one skilled in the art, and is dependent on a number of factors including age, sex, weigh, which the medical practitioner will be capable of determining.

In a preferred embodiment, sulindac is administered in doses of 5 mg to 400 mg, more preferably 50 mg to 300 mg, most preferably 150 mg to 200 mg. The lower limit for a dose is preferably 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg or 200 mg. The upper limit for a dose is preferably 400 mg, 390 mg, 380 mg, 370 mg, 360 mg, 350 mg, 340 mg, 330, mg, 320 mg, 310 mg, 300 mg, 290 mg, 280 mg, 270 mg, 260 mg, 250 mg, 240 mg, 230 mg, 220 mg or 210 mg. Any of the aforementioned lower or upper limits of the ranges may be combined with each other, and are herein disclosed. Preferably the dose is 150 mg to 200 mg.

Any of the above doses may be administered once a day, twice a day, three times a day or four times a day.

In an embodiment of the invention, sulindac is administered at least once a day. Preferably it is administered as a single daily dose. Preferably the single daily dose is of 200 mg to 400 mg. Preferably it is 200 mg, 300 mg or 400 mg.

In an embodiment of the invention, sulindac is administered twice daily. Preferably each dose is 150 mg to 200 mg, with a total daily dosage of 300 mg to 400 mg.

Alternatively, it may be administered three times per day. Preferably each dose is 100 mg to 130 mg.

Alternatively, it may be administered four times per day. Preferably each dose is 75 mg to 100 mg.

Preferably, the dosage regime is such that the total daily dosage of sulindac does not exceed 400 mg.

In order to treat fragile x syndrome, sulindac is used in a chronic dosage regime, i.e., chronic, long-term treatment.

The present invention also relates to use of sulindac, or a pharmaceutically acceptable salt thereof, for the manufacture of a medicament for use in the treatment of fragile x syndrome. This embodiment of the invention may have any of the preferred features described above.

The present invention also relates to a method of treating fragile x syndrome comprising administering to a subject in need thereof a therapeutically effective amount of sulindac or a pharmaceutically acceptable salt thereof. This embodiment of the invention may have any of the preferred features described above. The method of administration may be according to any of the routes described above.

For the avoidance of doubt, the present invention also embraces prodrugs which react in vivo to give a compound of the present invention.

The following study illustrates the invention.
Study 1
Animals

Fmr1 knockout 2 (Fmr1 KO2) mice were generated by deletion of the promoter and first exon of Fmr1. The Fmr1 KO2 it is both, protein and mRNA null. In this study we used Fmr1 KO2 and wild-type (WT) littermates generated on a C57BL/6J background and repeatedly backcrossed onto a C57BL/6J background for more than eight generations.
Animal Housing The Fmr1 KO2 mice were housed in 4-5 per cage groups of the same genotype in a temperature—(21±1° C.) and humidity-controlled room with a 12-hr light-dark cycle (lights on 7 a.m.-7 p.m.). Food and water were available ad libitum. Mice were housed in commercial plastic cages, and experiments were conducted in accordance with the requirements of the UK Animals (Scientific Procedures) Act, 1986. Protocols were reviewed and approved by the IEB, University of Chile Institute review board. All experiments were conducted with the staff blinded to genotype and drug treatment. Separate investigators prepared and coded the dosing solutions, allocated the mice to the study treatment groups, dosed the animals, and collected the behavioral data.
Treatment Groups There were four treatment groups per compound in the study with 10 male mice used per treatment group (all at 8 weeks of age): Group 1: Fmr1 KO2 mice treated with vehicle (Fmr1 KO2-V), Group 2: wild-type littermate mice treated with vehicle (WT-V), Group 3: Fmr1 KO2 mice treated with sulindac (Fmr1 KO-Sulindac) and Group 4: wild-type littermate mice treated with sulindac (WT-Sulindac)
Compound Information Sulindac was purchased from Sigma Aldrich. Synonym: (Z)-5-Fluoro-2-methyl-1-[p-(methylsulfinyl) benzylidene] indene-3-acetic acid.
Dosing Sulindac: 5 mg/kg by osmotic minipumps (ALZET Osmotic Pumps Cupertino, Calif., USA) implanted subcutaneously for 15 days delivery.
Behavioral Testing For experiments, all mice were tested once in the same apparatus. Prior to testing, mice were placed in the apparatus for some minutes before the experiment. The apparatus was cleaned with moist and dry tissues before testing each mouse. The aim was to create a low but constant background mouse odor for all experimental subjects. Testers were blind to the genotype and treatment during all testing and data analysis. We assessed weight loss, fur loss, walking, eyes open, eye discharges and general behavior. All signs indicated that all treatments were well tolerated by the Fmr1KO2 mice and WT littermates at all times.
Open Field (Hyperactivity)

The open-field apparatus was used to test hyperactivity. The apparatus was a gray PVC-enclosed arena 50×9×30 cm divided into a 10×10-cm grid. Mice were brought to the experimental room 5-20 min before testing. A mouse was placed into a corner square facing the corner and observed for 3 min. The number of squares entered by the whole body (locomotor activity) was counted. The movement of the mouse around the field was recorded with a video tracking device for 3 min (version NT4.0, Viewpoint).
Nesting The test was performed in individual cages. Normal bedding covered the floor to a depth of 0.5 cm. Each cage was supplied with a "Nestlet," a 5 cm square of pressed cotton batting (Ancare). Mice were placed individually into the nesting cages 1 hr. before the dark phase, and the results were assessed the next morning. Nest building was scored on a 5 point scale.

Score 1: The Nestlet was largely untouched (>90% intact).
Score 2: The Nestlet was partially torn up (50-90% remaining intact).
Score 3: The Nestlet was mostly shredded but often there was no identifiable nest site: <50% of the Nestlet
Score 4: An identifiable, but flat nest <90% of the Nestlet was torn up, the material was gathered into a flat nest with walls higher than the mouse height curled up on its side) on less than 50% of its circumference.
Score 5: A (near) perfect nest: >90% of the Nestlet was torn up, the nest was a crater, with walls higher than mouse body height on more than 50% of its circumference.
Fear Conditioning The dependent measure used in contextual fear conditioning was a freezing response following a pairing of an unconditioned stimulus (foot shock), with a conditioned stimulus, a particular context. Freezing is a species-specific response to fear, which has been defined as "absence of movement except for respiration". This may last for seconds to minutes depending on the strength of the aversive stimulus, the number of presentations, and the degree of learning achieved by the subject. Testing involved placing the animal in a novel environment (dark chamber), providing an aversive stimulus (a 1-sec electric shock, 0.2 mA, to the paws), and then removing it.

Social Interaction

In the three-chambered sociability task, a subject mouse was evaluated for its exploration of a novel social stimulus (novel mouse). The three-chambered social approach task monitors direct social approach behaviors when a subject mouse is presented with the choice of spending time with either a novel mouse or an empty cup. Sociability is defined as the subject mouse spending more time in the chamber containing the mouse than in the empty chamber. Preference for social novelty is defined as spending more time in the chamber with the novel mouse. The apparatus is a rectangular three-chamber box, where each chamber measures 20 cm (length)×40.5 cm (width)×22 cm (height). Dividing walls are made from clear perplex, with small openings (10 cm width×5 cm height) that allow access into each chamber. The three chamber task was lit from below (10 lux). The mice were allowed to freely explore the three-chamber apparatus over three 10 min trials. During the trial one wire cup was placed upside down in one of the side chambers and a novel mouse was placed under another wire cup in the other side chamber (novel mouse stimulus), leaving the middle chamber empty. The location of the novel mouse across trials was counterbalanced to minimize any potential confound due to a preference for chamber location. The time spent exploring the novel mice was scored as exploration ratio.

Statistical Analysis of Behavioral Data

Data were analyzed by two-way analysis of variance (ANOVA) followed by post-test comparisons where appropriate using Tukey's Multiple Comparison Test. Data are represented as the mean and standard error of the mean (SEM). Statistical analyses were performed in GraphPad Prism 7.03. From FIG. 1A-FIG. 1D it can be see that:

A. Fifteen-day chronic treatment with sulindac normalizes hyperactivity displayed by the Fmr1 KO2 mice.

B. Fmr1 KO2 mice treated with sulindac showed normalization in nesting behavior.

C. In the contextual memory test, freezing was reduced in Fmr1 KO2 mice when compared to freezing of WT littermates. Treatment with Sulindac ameliorates the Fmr1 KO deficit in learning and memory (KO not different from WT, $p=0.3968$).

D. Fmr1 KO2 mice showed a significantly lower exploration index of the novel mouse compared to WT mice ($p<0.005$), indicating impaired sociability. Sulindac partially improved such impairment in Fmr1 KO2 mice.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of treating fragile x syndrome comprising administering to a subject in need thereof a therapeutically effective amount of sulindac or a pharmaceutically acceptable salt thereof.

2. The method of claim 1, wherein the subject is human.

3. The method of claim 1, wherein a dose of 50 mg to 400 mg of sulindac is administered.

4. The method of claim 1, wherein a dose of 50 mg to 300 mg of sulindac is administered.

5. The method of claim 1, wherein a dose of 150 mg to 200 mg of sulindac is administered.

6. The method of claim 1, wherein a dose of sulindac is administered once per day.

7. The method of claim 1, wherein a dose of 300 mg to 400 mg of sulindac is administered once per day.

8. The method of claim 1, wherein a dose of sulindac is administered twice per day.

9. The method of claim 1, wherein a dose of 150 mg to 200 mg of sulindac is administered twice per day.

10. The method of claim 1, wherein sulindac is administered orally.

11. The method of claim 1, wherein sulindac is administered parenterally, transdermally, sublingually, rectally, or by inhalation.

12. The method of claim 1, wherein the subject exhibits signs of hyperactivity, social anxiety, memory loss, or disruptive behaviour.

13. The method of claim 1, wherein the subject exhibits signs of hyperactivity, memory loss, or disruptive behaviour.

14. The method of claim 1, wherein the subject is human; and a dose of 300 mg to 400 mg of sulindac is administered once per day.

15. The method of claim 1, wherein the subject is human; and a dose of 150 mg to 200 mg of sulindac is administered twice per day.

16. The method of claim 1, wherein the subject is human; and a dose of 300 mg to 400 mg of sulindac is administered orally once per day.

17. The method of claim 1, wherein the subject is human; and a dose of 150 mg to 200 mg of sulindac is administered orally twice per day.

* * * * *